United States Patent [19]

Godschalx et al.

[11] Patent Number: 4,782,178

[45] Date of Patent: Nov. 1, 1988

[54] HALOGENATED PHENYL CYANATES

[75] Inventors: James P. Godschalx; Murray Daniel J.; Abel Mendoza, all of Midland, Mich.

[73] Assignee: The Dow Chemical Company, Midland, Mich.

[21] Appl. No.: 120,310

[22] Filed: Nov. 13, 1987

[51] Int. Cl.$^4$ .......................................... C07C 122/00
[52] U.S. Cl. .................................. 560/301; 558/422; 558/421
[58] Field of Search ................. 560/301; 558/422, 421

[56] References Cited

PUBLICATIONS

Korshak, et al., Polymer Science USSR, A17, No. 1, pp. 23–27, 1975.
Brand et al., NASA Contractor Report 3185, 1979.
Grigat et al., Table 1, Angew. Chem. 79. 219 (1967).

*Primary Examiner*—Alan L. Rotman
*Assistant Examiner*—Robert C. Whittenbaugh

[57] ABSTRACT

Phenyl cyanates substituted at both ortho positions and further substituted with at least one halo at the meta or para positions are prepared. Then enhance ignition resistance, fire retardance, and toughness of polytriazines when added in varying amounts to polycyanate monomers before cure.

13 Claims, No Drawings

HALOGENATED PHENYL CYANATES

BACKGROUND OF THE INVENTION

This invention relates to halogenated phenyl cyanates. More particularly, it relates to halogenated phenyl cyanates substituted at both ortho positions.

Phenyl cyanate and phenyl cyanate substituted at the para position have been used as reactive additives to modify polymers of polycyanate monomers. Polycyanate monomers are known thermosets that polymerize to form polytriazines. Korshak et al., *Polymer Science USSR*, A17: No. 1, p. 23-27, 1975, disclose modified physical and mechanical properties of a polytriazine prepared from the dicyanate of bisphenol A and varying amounts of phenyl cyanate. Brand et al., *NASA Contractor Report* 3185, 1979, disclose reduced water sorption of polytriazines prepared from dicyanates and varying amounts of either 4-nonylphenyl cyanate or 4-phenylphenyl cyanate.

Unfortunately, even though the addition of the phenyl cyanates employed in the art reduces water sorption of the prepared polytriazine, other physical and mechanical properties of the polytriazine are adversely affected. More significantly, Korshak et al., supra, disclose a significant reduction in toughness, as measured by impact strength, relative to a polytriazine prepared without the addition of a phenyl cyanate.

In view of the deficiencies of the prior art, a phenyl cyanate is needed that does not adversely affect physical and mechanical properties of prepared polytriazines. Moreover, a phenyl cyanate is needed that enhances these properties, especially those properties relating to toughness and flame retardance.

SUMMARY OF THE INVENTION

The invention is a halogenated phenyl cyanate of the formula:

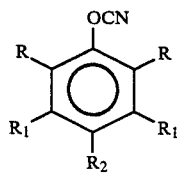

wherein each R is independently straight or branched $C_{1-4}$ alkyl, $X-CH_2-$, $Y-OCH_2-$, $Y-SCH_2-$, $Y-COCH_2-$, or $Y-COOCH_2-$; each $R_1$ is independently hydrogen, halo, $C_{1-4}$ alkyl, $C_{1-4}$ alkoxy or thioalkoxy, or cyano; $R_2$ is hydrogen, halo, straight or branched $C_{1-4}$ alkyl, phenyl or substituted phenyl, mercapto, cyano, formyl, $Y-O-$, $Y-S-$, $Y-CO-$, $Y-COO-$, $X-CH_2-$, $Y-OCH_2-$, $Y-SCH_2-$, $Y-COCH_2-$, or $Y-COOCH_2-$; X is halo, phenyl or substituted phenyl, mercapto, formyl, or cyano; and Y is $C_{1-4}$ alkyl, or phenyl or substituted phenyl; provided at least one $R_1$ or $R_2$ is halo.

Surprisingly, the halogenated phenyl cyanates of this invention improve toughness, fire retardance, and ignition resistance of polytriazines when added in varying amounts to polycyanate monomers before cure. The halogenated phenyl cyanates are useful as reactive additives for enhancing these properties as well as other physical and mechanical properties of polytriazines.

DETAILED DESCRIPTION

The phenyl cyanates of this invention are substituted at both ortho positions and further substituted with at least one halo at the meta or para position. They can be represented by the following formula:

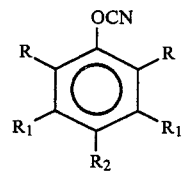

wherein each R is independently straight or branched $C_{1-4}$ alkyl, $X-CH_2-$, $Y-OCH_2-$, $Y-SCH_2-$, $Y-COCH_2-$, or $Y-COOCH_2-$; ach $R_1$ is independently hydrogen, halo, $C_{1-4}$ alkyl, $C_{1-4}$ alkoxy or thioalkoxy (i.e., alkylthio), or cyano; $R_2$ is hydrogen, halo, straight or branched $C_{1-4}$ alkyl, phenyl or substituted phenyl, mercapto, cyano, formyl, $Y-O-$, $Y-S-$, $Y-CO-$, $Y-COO-$, $X-CH_2-$, $Y-OCH_2-$, $Y-SCH_2-$, $Y-COCH_2-$, or $Y-COOCH_2-$; X is halo, phenyl or substituted phenyl, mercapto, formyl, or cyano; and Y is $C_{1-4}$ alkyl, or phenyl or substituted phenyl; provided at least one $R_1$ or $R_2$ is halo.

"Substituted phenyl" refers to phenyl substituted with halo or methyl, or any other substituent that does not adversely affect the properties of the prepared polytriazine.

Examples of halogenated phenyl cyanates within the scope of this invention are 2,4,6-trimethyl-3,5-dibromophenyl cyanate; 2,6-dimethyl-3,4,5-tribromophenyl cyanate; 2,6-disec-butyl-3,4,5;1-tribromophenyl cyanate; 2,4,6-triisopropyl-3-chlorophenyl cyanate; 2-methoxymethyl-4,6-dimethyl-3,5-dibromophenyl cyanate; 2,3,6-trimethyl-4-bromophenyl cyanate; 4-methoxymethyl-2,6-dimethyl-3,5-dibromophenyl cyanate; 4-acetoxymethyl-2,6-dimethyl-3,5-dibromophenyl cyanate; 2-acetoxymethyl-4,6-dimethyl-3,5-dibromophenyl cyanate; 4-cyanomethyl-2,6-dimethyl-3,5-dibromophenyl cyanate; 4-bromomethyl-2,6-dimethyl-3,5-dibromophenyl cyanate; 2,6-dimethyl-3-methoxy-5-cyano-4-bromophenyl cyanate; and 2,6-dibenzyl-4-phenyloxy-3,5-dibromophenyl cyanate.

A more preferred class of halogenated phenyl cyanates is represented by the formula:

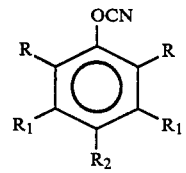

wherein each R is independently straight or branched $C_{1-4}$ alkyl, $X-CH_2-$, $Y-OCH_2-$; or $Y-COOCH_2-$; each $R_1$ is independently hydrogen, halo, $C_{1-4}$ alkyl, $C_{1-4}$ alkoxy or thioalkoxy, or cyano; each $R_2$ is hydrogen, halo, straight or branched $C_{1-4}$ alkyl, phenyl or substituted phenyl, cyano, $Y-O-$, $X-CH_2-$, $Y-OCH_2-$, or $Y-COOCH_2-$; X is halo, phenyl, or substituted phenyl or cyano; Y is $C_{1-4}$ alkyl, or phenyl or substituted phenyl; provided at least one $R_1$ or $R_2$ is halo.

Preferred straight or branched $C_{1-4}$ alkyl are methyl, secondary or tertiary butyl, and isopropyl, and the halogenated phenyl cyanates are represented by the formula:

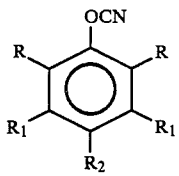

wherein each R is independently methyl, methoxymethyl, acetoxymethyl, secondary or tertiary butyl, or isopropyl; each $R_1$ is independently hydrogen, halo, methyl, methoxy, or cyano; and $R_2$ is hydrogen, halo, methyl, methoxymethyl, acetoxymethyl, secondary or tertiary butyl, isopropyl, methoxy, cyano, phenyl, phenyloxy, or benzyl; provided at least one $R_1$ or $R_2$ is halo.

An even more preferred class is represented by the formula:

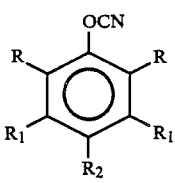

wherein each R is independently methyl, methoxymethyl, acetoxymethyl, secondary or tertiary butyl, or isopropyl; each $R_1$ is independently hydrogen, halo, or methyl; and $R_2$ is hydrogen, halo, methyl, methoxymethyl, acetoxymethyl, secondary or tertiary butyl or isopropyl; provided at least one $R_1$ or $R_2$ is halo.

Preferably, the class of substituents at the para position is limited to the preferred class of substituents at the meta positions, and the phenyl cyanate is represented by the formula:

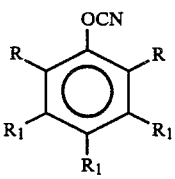

wherein each R is independently methyl, methoxymethyl, acetoxymethyl, secondary butyl, or isopropyl; and each $R_1$ is independently hydrogen, chloro, bromo, or methyl; provided at least one $R_1$ is chloro or bromo.

The preferred substituents at the meta and para positions are hydrogen, bromo, and methyl; and the phenyl cyanate is represented by the formula:

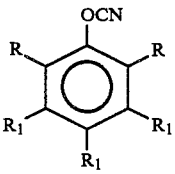

wherein each R is independently methyl, methoxymethyl, acetoxymethyl, secondary butyl, or isopropyl; and each $R_1$ is independently hydrogen, bromo, or methyl; provided at least one $R_1$ is bromo.

A more preferred class of phenyl cyanates is represented by the formula:

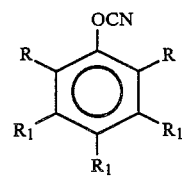

wherein each R is independently methyl, methoxymethyl, secondary butyl, or isopropyl; and each $R_1$ is independently hydrogen, bromo, or methyl; provided at least one $R_1$ is bromo.

The most preferred class of phenyl cyanates is depicted when both ortho positions are substituted with methyl, isopropyl, or secondary butyl. The class is represented by the formula:

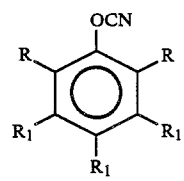

wherein R is methyl, isopropyl, or secondary butyl; and each $R_1$ is independently hydrogen, bromo, or methyl; provided at least one $R_1$ is bromo.

Preferably, each meta position and the para position is independently substituted with bromo or methyl, and the class of phenyl cyanates is represented by the formula:

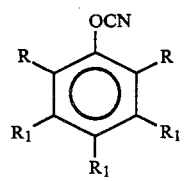

wherein R is methyl, isopropyl, or secondary butyl; and each $R_1$ is independently bromo or methyl, provided at least one $R_1$ is bromo.

The most preferred halogenated phenyl cyanates are depicted when both ortho substituents are methyl and both meta substituents are bromo. These cyanates are represented by the formula:

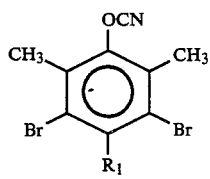

wherein $R_1$ is bromo or methyl.

The most preferred halogenated phenyl cyanates are 2,4,6-trimethyl-3,5-dibromophenyl cyanate, which is represented by the formula:

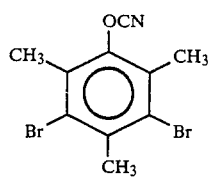

and 2,6-dimethyl-3,4,5-tribromophenyl cyanate, which is represented by the formula:

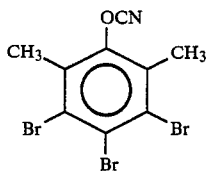

In one embodiment, the halogenated phenyl cyanates of this invention can be prepared by reacting the corresponding halogenated phenol with a cyanogen halide in the presence of an acid scavenger at a temperature between about −25° C. and about −30° C. Preferably, a solution of the halogenated phenol in methylene chloride and triethylamine is added to a cooled solution of the cyanogen halide in methylene chloride at a rate sufficient to maintain reaction temperature. Equimolar or a slight molar excess of the cyanogen halide and triethylamine are desired. Reaction temperatures above about −25° C. may cause undesirable byproduct formation; temperatures below about −30° C. may decrease the reaction rate. The prepared phenyl cyanate may be separated from the reaction product mixture by first washing with a dilute aqueous solution of hydrochloric acid to remove excess cyanogen halide and triethylamine salt and then removing the solvent in vacuo.

In another embodiment, if the corresponding halogenated phenol has a substituent on the ring that reacts with the acid scavenger, then the halogenated phenyl cyanate can be prepared by first converting the reactive substituent to an inert substituent before reacting the phenol with a cyanogen halide as described above. After the reaction, the inert substituent can be converted back to the original reactive substituent. As an example, the following illustrates the preparation of a brominated phenyl cyanate substituted at the para position with bromomethyl (the bromomethyl substituent is known to react with acid scavengers such as triethylamine):

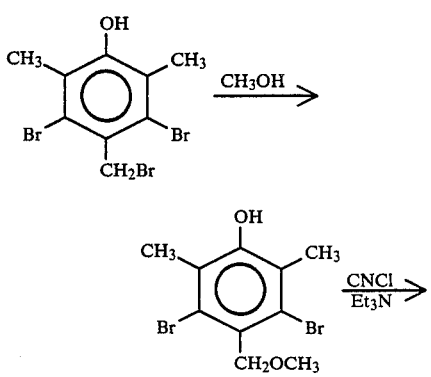

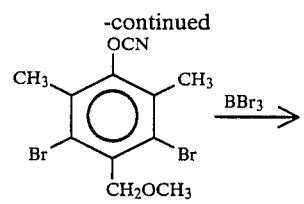

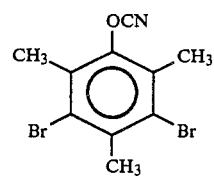

Processes for halogenating phenols, particularly phenols substituted at both ortho positions, is well known in the art and disclosed in U.S. Pat. No. 4,684,752; Jacquesy et al., *J. C. S. Chem. Comm.*, 110–111 (1980); Semsarzadeh et al., *Macromolecules*, 10, 482–485 (1977); Fischer et al., *Can J. Chem.*, 61, 1045–1052 (1983); Fischer et al., *J. C. S. Chem. Comm.*, 279–280 (1979); and Van Der Meer, *Rec. Trav. Chim.*, 63, 147–156 (1944).

Although the mechanism by which the reactive phenyl cyanates of this invention increase toughness of polytriazines is unclear, it is believed that the ortho substituents of the phenyl cyanate hinder reaction of the phenyl cyanate with itself and thus allow increased reaction with the polycyanate monomer. The reaction between the phenyl cyanate and the polycyanate monomer reduces the crosslink density of the prepared polytriazine and increases toughness.

The reactive halogenated phenyl cyanates enhance the fire retardant properties of polytriazines by incorporating therein an increased halogen content relative to the unmodified polytriazine.

The following examples illustrate but do not limit the scope of this invention.

EXAMPLE 1

Preparation of 2,4,6-trimethyl-3,5-Dibromophenyl Cyanate

Twenty milliliters (ml) of methylene chloride are added to a 100 ml, 3-neck roundbottom flask fitted with a thermometer, pressure equalizing dropping funnel and nitrogen inlet. The flask is cooled in a bath of dry ice and ethylene glycol until the methylene chloride reaches a temperature of −30° C. Cyanogen bromide (4.32 grams (g), 0.0408 moles) is added to the flask. A solution of 2,4,6-trimethyl-3,5-dibromophenol (10.0 g, 0.034 mole), triethylamine (3.96 g, 0.0391 mole), and 20 ml of methylene chloride is added dropwise through the dropping funnel over a 1-hour period. The reaction temperature is maintained between −25° C. and −30° C. After about ⅔ of the phenol solution is added, a solid begins to precipitate. When the addition of the phenol solution is complete, the dropping funnel is rinsed with an additional 5 ml of methylene chloride. The reaction mixture is stirred at −30° C. for 45 minutes and then is allowed to warm to room temperature over an additional 45 minutes. 0.1N aqueous HCl is added to the reaction mixture to neutralize excess cyanogen bromide and the mixture is then stirred for 5 minutes. The neutralized mixture is transferred to a separatory funnel and the organic layer is removed. The organic layer is washed with water and is dried over magnesium sulfate. The solvent is removed from the treated organic layer in vacuo to give 10.9 g of a white solid (100 percent crude yield). This material is heated to 75° C. under vacuum to remove volatiles. The material is then bulb to bulb distilled at 150° C. and 0.1 millimeters (mm) mercury to give a white solid (7.46 g, 69 percent yield) with a melting point between 126.5° and 127.5° C.

Analysis by means of NMR yields $^1$H-NMR (CDCl$_3$)δ=2.40(s, 6H), 2.60 (s, 3H).

$^{13}$C-NMR (CDCl$_3$)δ=17.59, 25.61, 109.69, 125.74, 128.72, 138.20, 148.40.

EXAMPLE 2

Preparation of Polytriazines From a Polycyanate Monomer and 2,4,6-Trimethyl-3,5-Dibromophenyl Cyanate For each of a series of runs, a beaker containing 100 g of a polycyanate monomer is heated to 85° C. The monomer is represented by the formula:

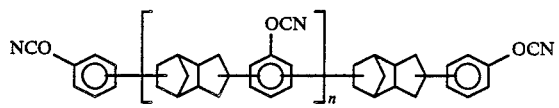

wherein n has an average value of 0.2 Varying amounts of 2,4,6-trimethyl-3,5-dibromophenyl cyanate and 100 ppm of cobalt as cobalt acetylacetonate are added to the beaker. The mixture is heated to 105° C. and mixed until homogeneous. Boiling stones are added and the mixture is degassed in a vacuum oven at 150° C. for 30 minutes. The mixture is then poured into preheated parallel plate molds having mold cavities of ⅛-inch thick. The mixture is cured for 1 hour at 175° C., 2 hours at 225° C. and 1 hour at 250° C. After curing, the mold is allowed to cool slowly to room temperature. The mold is opened and a solid plaque is removed. The plaque is then cut and analyzed.

The flame retardance of the modified polytriazine for each run is illustrated in Table I

TABLE I

Flame Retardance of Polytriazines Prepared From a Polycyanate Monomer and Varying Amounts of a Preferred Phenyl Cyanate

| Weight Percent of the Phenyl Cyanate in Mixture of the Phenyl Cyanate and Polycyanate Monomer | Calculated Weight Percent of Bromine in Mixture | Total Burn Time[2] of Modified Polytriazine (seconds) | UL-94 Rating[1] of Modified Polytriazine |
|---|---|---|---|
| 10 | 5 | 170 | HB |
| 12 | 6 | 43 | V-O |
| 15 | 7.5 | 8 | V-O |

[1]UL-94 rating is the rating specified by Underwriters Laboratory Test No. 94
[2]Total Burn Time is determined from procedures specified in the UL-94 test.

The data in Table I indicate the enhanced flame retardance of a polytriazine when a sufficient amount of a halogenated phenyl cyanate of this invention is added to a polycyanate monomer before cure. The modified polytriazine exhibits a V-O rating when it contains a sufficient bromine content.

The toughness of the modified polytriazine for each run is illustrated in Table II.

TABLE II

Toughness of Polytriazines Prepared From a Polycyanate Monomer and Varying Amounts of a Preferred Phenyl Cyanate

| Weight Percent of the Phenyl Cyanate in Mixture of the Phenyl Cyanate and Polycyanate Monomer | $G_{IC}$[1] (J/m$^2$) of Modified Polytriazine |
|---|---|
| 0* | 60 |
| 9.6 | 115 |
| 13.0 | 133 |

*Not an example of this invention.
[1]$G_{IC}$ is the fracture energy as measured by compact tension according to ASTM Procedure E-399

The data clearly indicates increased toughness, as measured by fracture energy, for polytriazines modified with a phenyl cyanate of this invention.

What is claimed is:

1. A halogenated phenyl cyanate of the formula:

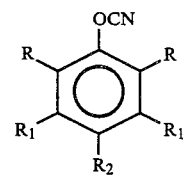

wherein
each R is independently straight or branched C$_{1-4}$ alkyl, X—C$_2$—, Y—OCH$_2$—, Y—SCH$_2$—, Y—COCH$_2$—, or Y—COOCH$_2$—;
each R$_1$ is independently hydrogen, halo, C$_{1-4}$ alkyl, C$_{1-4}$ alkoxy or thioalkoxy, or cyano;
R$_2$ is hydrogen, halo, straight or branched C$_{1-4}$ alkyl, phenyl or phenyl substituted with halo or methyl, mercapto, cyano, formyl, Y—O—, Y—S—, Y—CO—, Y—COO—, X—CH$_2$—, Y—OCH$_2$—, Y—SCH$_2$—, Y—COCH$_2$—, or Y—COOCH$_2$—;
X is halo, phenyl or phenyl substituted with halo or methyl, mercapto, formyl, or cyano; and
Y is C$_{1-4}$ alkyl, or phenyl or phenyl substituted with halo or methyl; provided at least one R$_1$ or R$_2$ is halo.

2. The phenyl cyanate of claim 1 of the formula:

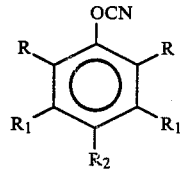

wherein
each R is independently straight or branched C$_{1-4}$ alkyl, X—CH$_2$—, Y—OCH$_2$—, or Y—COOCH$_2$—;
each R$_1$ is independently hydrogen, halo, C$_{1-4}$ alkyl, C$_{1-4}$ alkoxy or thioalkoxy, or cyano;
each R$_2$ is hydrogen, halo, straight or branched C$_{1-4}$ alkyl, phenyl or phenyl substituted with halo or methyl, cyano, Y—O—, X—CH$_2$—, Y—OCH$_2$— or Y—COOCH$_2$—;

X is halo, phenyl or phenyl substituted with halo or methyl, or cyano;

Y is $C_{1-4}$ alkyl, or phenyl or phenyl substituted with halo or methyl; provided at least one $R_1$ or $R_2$ is halo.

3. The phenyl cyanate of claim 2 of the formula:

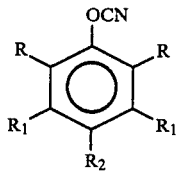

wherein
  each R is independently methyl, methoxymethyl, acetoxymethyl, secondary or tertiary butyl, or isopropyl;
  each $R_1$ is independently hydrogen, halo, methyl, methoxy, or cyano; and
  $R_2$ is hydrogen, halo, methyl, methoxymethyl, acetoxymethyl, secondary or tertiary butyl, isopropyl, methoxy, cyano, phenyl, phenyloxy, or benzyl; provided at least one $R_1$ or $R_2$ is halo.

4. The phenyl cyanate of claim 3 of the formula:

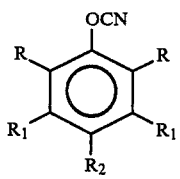

wherein
  each R is independently methyl, methoxymethyl, acetoxymethyl, secondary or tertiary butyl, or isopropyl;
  each $R_1$ is independently hydrogen, halo, or methyl; and
  $R_2$ is hydrogen, halo, methyl, methoxymethyl, acetoxymethyl, secondary or tertiary butyl, or isopropyl;
provided at least one $R_1$ or $R_2$ is halo.

5. The phenyl cyanate of claim 4 wherein halo is chloro or bromo.

6. The phenyl cyanate of claim 5 of the formula:

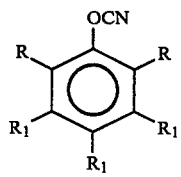

wherein
  each R is independently methyl, methoxymethyl, acetoxymethyl, secondary butyl, or isopropyl; and
  each $R_1$ is independently hydrogen, chloro, bromo, or methyl;
provided at least one $R_1$ is chloro or bromo.

7. The phenyl cyanate of claim 6 of the formula:

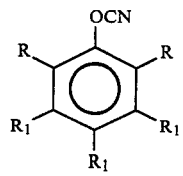

wherein
  each R is independently methyl, methoxymethyl, acetoxymethyl, secondary butyl, or isopropyl; and
  each $R_1$ is independently hydrogen, bromo, or methyl;
provided at least one $R_1$ is bromo.

8. The phenyl cyanate of claim 7 of the formula:

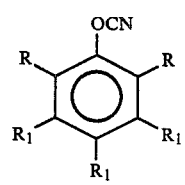

wherein
  each R is independently methyl, methoxymethyl, secondary butyl, or isopropyl; and
  each $R_1$ is independently hydrogen, bromo, or methyl;
provided at least one $R_1$ is bromo.

9. The phenyl cyanate of claim 8 of the formula:

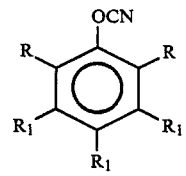

wherein
  R is methyl, isopropyl, or secondary butyl; and
  each $R_1$ is independently hydrogen, bromo, or methyl;
provided at least one $R_1$ is bromo.

10. The phenyl cyanate of claim 9 of the formula:

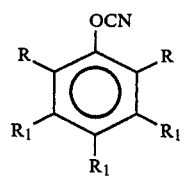

wherein
  R is methyl, isopropyl, or secondary butyl; and
  each $R_1$ is independently bromo or methyl;
provided at least one $R_1$ is bromo.

11. The phenyl cyanate of claim 10 of the formula:

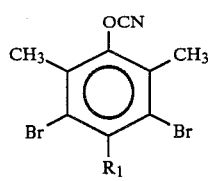
wherein R₁ is bromo or methyl.
12. The phenyl cyanate of claim 11 of the formula:
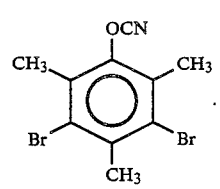
13. The phenyl cyanate of claim 11 of the formula:
[structure: benzene ring with OCN at top, CH₃ at positions 2 and 6, Br at positions 3 and 5, CH₃ at position 4]
* * * * *

UNITED STATES PATENT AND TRADEMARK OFFICE
CERTIFICATE OF CORRECTION

PATENT NO. : 4,782,178

DATED : November 01,1988

INVENTOR(S) : James Godschalx et al

It is certified that error appears in the above-identified patent and that said Letters Patent is hereby corrected as shown below:

Cover page [75] "Murray Daniel J.;" should read --Daniel J. Murray;--
Cover page, [57] ABSTRACT, Line 3, "Then" should read --They--
Column 1, line 26, " More" should read --Most--
Column 2, line 35, "2,6-disec-butyl-3,4,5,;1" should read
$\qquad$ --2,6-disec-butyl-3,4,5;--
Column 8, line 35, "X-C$_2$-," should read --X-CH$_2$-,--

Signed and Sealed this

Eighth Day of May, 1990

Attest:

HARRY F. MANBECK, JR.

Attesting Officer

Commissioner of Patents and Trademarks